(12) United States Patent
Luo et al.

(10) Patent No.: US 12,343,440 B2
(45) Date of Patent: Jul. 1, 2025

(54) DISPLAY MODULE AND ELECTRONIC DEVICE

(71) Applicant: HKC Corporation Limited, Guangdong (CN)

(72) Inventors: Fei Luo, Guangdong (CN); Rongrong Li, Guangdong (CN)

(73) Assignee: HKC CORPORATION LIMITED, Guangdong (CN)

( * ) Notice: Subject to any disclaimer, the term of this patent is extended or adjusted under 35 U.S.C. 154(b) by 0 days.

(21) Appl. No.: 18/509,573

(22) Filed: Nov. 15, 2023

(65) Prior Publication Data

US 2024/0316233 A1  Sep. 26, 2024

(30) Foreign Application Priority Data

Mar. 23, 2023 (CN) .......................... 202310287257.9

(51) Int. Cl.
  *A61L 2/10* (2006.01)
  *A61L 2/24* (2006.01)
  *G06F 3/041* (2006.01)

(52) U.S. Cl.
  CPC ........ *A61L 2/10* (2013.01); *A61L 2/24* (2013.01); *G06F 3/0412* (2013.01)

(58) Field of Classification Search
  CPC .............. A61L 2/10; A61L 2/24; G06F 3/0412
  See application file for complete search history.

(56) References Cited

U.S. PATENT DOCUMENTS

| | | |
|---|---|---|
| 2013/0045132 A1 | 2/2013 | Tumanov |
| 2021/0000991 A1 | 1/2021 | Kraus et al. |

(Continued)

FOREIGN PATENT DOCUMENTS

| | | |
|---|---|---|
| CN | 110319928 A | 10/2019 |
| CN | 111538442 A | 8/2020 |

(Continued)

OTHER PUBLICATIONS

Chen et al., "Comparison of the disinfection effect of two different disinfection methods on dental handpieces", Practical Preventive Medicine (Dec. 2002), vol. 9, No. 6, retrieved from: https://xueshu.baidu.com/usercenter/paper/show?paperid=75847374845ee77c430bea6b518c6e97&site=xueshu_se.

(Continued)

*Primary Examiner* — Regina M Yoo

(74) *Attorney, Agent, or Firm* — Scully, Scott, Murphy & Presser, P.C.

(57) ABSTRACT

A display module and an electronic device are provided. The display module includes a display panel and a backlight module stacked with the display panel. The backlight module includes a back plate, a light-emitting member. The back plate has a bottom wall and a plurality of side walls, the plurality of side walls surround the bottom wall to define an accommodation space. The light-emitting member is accommodated in the accommodation space and carried on the bottom wall, and the light-emitting member is configured to emit visible light. The display module further includes an ultraviolet (UV)-ray emitting assembly. The UV-ray emitting assembly is accommodated in the accommodation space and disposed corresponding to one of plurality of the side walls, and the UV-ray emitting assembly is obliquely disposed with respect to the display panel and configured to emit UV rays to the display panel.

18 Claims, 7 Drawing Sheets

(56) References Cited

U.S. PATENT DOCUMENTS

| | | | |
|---|---|---|---|
| 2021/0196848 A1 | 7/2021 | Baarman | |
| 2022/0088243 A1 | 3/2022 | Takahata | |
| 2023/0128052 A1* | 4/2023 | Baarman | A61L 2/24 |
| | | | 250/454.11 |

FOREIGN PATENT DOCUMENTS

| | | |
|---|---|---|
| CN | 112416182 A | 2/2021 |
| CN | 213251504 U | 5/2021 |
| CN | 113589586 A | 11/2021 |
| CN | 113721791 A | 11/2021 |
| CN | 114099750 A | 3/2022 |
| CN | 115177754 A | 10/2022 |
| TW | M478860 U | 5/2014 |
| WO | WO-2019241112 A1 * 12/2019 | ............... A61L 2/10 |

OTHER PUBLICATIONS

Chinese First Office Action dated Apr. 28, 2023 issued in CN 202310287257.9.

Notice of Allowance dated May 9, 2023 issued in CN 202310287257.9.

\* cited by examiner ined States Patent

DISPLAY MODULE AND ELECTRONIC DEVICE

CROSS-REFERENCE TO RELATED APPLICATION

This application claims priority under 35 U.S.C. § 119(a) to Chinese Patent Application No. 2023102872579, filed Mar. 23, 2023, the entire disclosure of which is incorporated herein by reference.

TECHNICAL FIELD

This disclosure relates to the field of display device technologies, and in particular, to a display module and an electronic device.

BACKGROUND

With the development of artificial intelligence technologies, touch screens are becoming more and more popular in various fields such as office, scientific research, medical, in-vehicle, and aerospace.

However, since the touch screen is prone to breeding a large amount of viruses, bacteria, and the like due to touch of a user, especially public touch screens are used by many users, and are more likely to breed viruses and bacteria, which may have negative effect on users with weakened immune systems.

SUMMARY

In a first aspect, a display module including a display panel and a backlight module stacked with the display panel. The backlight module includes a back plate and a light-emitting member. The back plate has a bottom wall and multiple side walls, and the multiple side walls surround the bottom wall to define an accommodation space. The light-emitting member is accommodated in the accommodation space and carried on the bottom wall, and the light-emitting member is configured to emit visible light. The display module further include an ultraviolet (UV)-ray emitting assembly accommodated in the accommodation space and disposed corresponding to one of plurality of the side walls. The UV-ray emitting assembly is obliquely disposed with respect to the display panel and configured to emit UV rays from a side facing away from a display surface of the display panel to the display panel so as to disinfect the display surface of the display panel and air at a side of the display surface of the display panel.

In a second aspect, an electronic device is provided. The electronic device includes a processor and a display module. The display module includes a display panel and a backlight module stacked with the display panel. The backlight module includes a back plate and a light-emitting member. The back plate has a bottom wall and multiple side walls, and the multiple side walls surround the bottom wall to define an accommodation space. The light-emitting member is accommodated in the accommodation space and carried on the bottom wall, and the light-emitting member is configured to emit visible light. The display module further include an ultraviolet (UV)-ray emitting assembly accommodated in the accommodation space and disposed corresponding to one of plurality of the side walls. The UV-ray emitting assembly is obliquely disposed with respect to the display panel and configured to emit UV rays from a side facing away from a display surface of the display panel to the display panel so as to disinfect the display surface of the display panel and air at a side of the display surface of the display panel. The processor is electrically connected to the UV-ray emitting assembly in the display module and is configured to control the UV-ray emitting assembly.

BRIEF DESCRIPTION OF THE DRAWINGS

To explain technical solutions in implementations of the present disclosure more clearly, the following will give a brief introduction to accompanying drawings which are needed to be used in description of implementations. Apparently, the accompanying drawings described herein are merely some implementations of the present disclosure, and a person of ordinary skill in the art may still derive other drawings from these accompanying drawings without creative efforts.

DETAILED DESCRIPTION

Technical solutions of implementations of the present disclosure will be described clearly and completely with reference to accompanying drawings in implementations of the present disclosure. Apparently, implementations described herein are merely some implementations, rather than all implementations, of the present disclosure. Based on implementations of the present disclosure, all other implementations obtained by those of ordinary skill in the art without creative effort shall fall within the protection scope of the present disclosure.

Terms "first", "second", and the like used in the specification, the claims, and the accompany drawings of the present disclosure are used to distinguish different objects rather than describe a particular order. In addition, the terms "include", "comprise", and "have" as well as variations thereof are intended to cover non-exclusive inclusion. For example, a process, a method, a system, a product, or a device including a series of operations or units is not limited to the listed operations or units, it can optionally include other operations or units that are not listed; alternatively, other operations or units inherent to the process, the method, the product, or the device can be included either.

A term "implementation" referred to herein means that a particular feature, structure, or characteristic described in conjunction with implementations may be contained in at least one implementation of the present disclosure. The phrase appearing in various places in the specification does not necessarily refer to the same implementation, nor does it refer an independent or alternative implementation that is mutually exclusive with other implementations. It is expressly and implicitly understood by those skilled in the art that an implementation described herein may be combined with other implementations.

Figure 1:
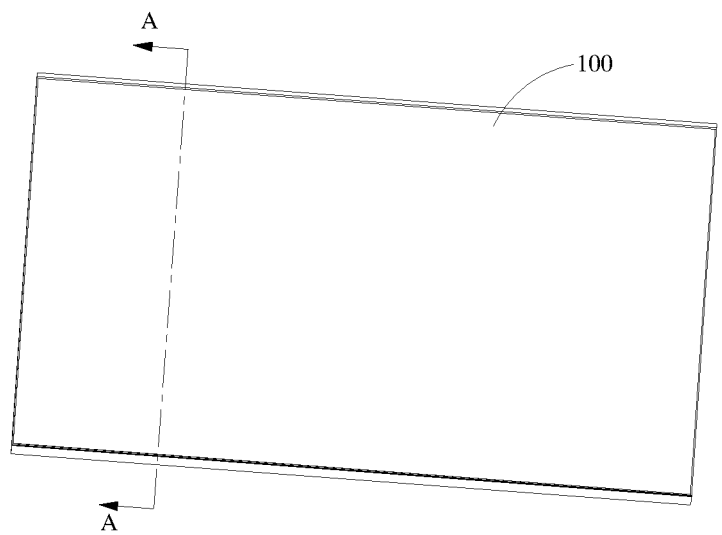
FIG. 1 is a schematic structural view of a display module provided in an implementation of the present disclosure.
Figure 2:
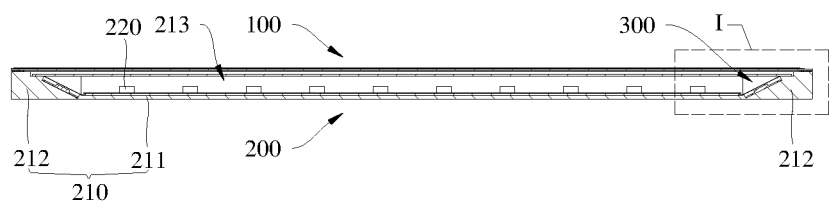
FIG. 2 is a schematic cross-sectional view taken along line A-A in FIG. 1.
Figure 3:
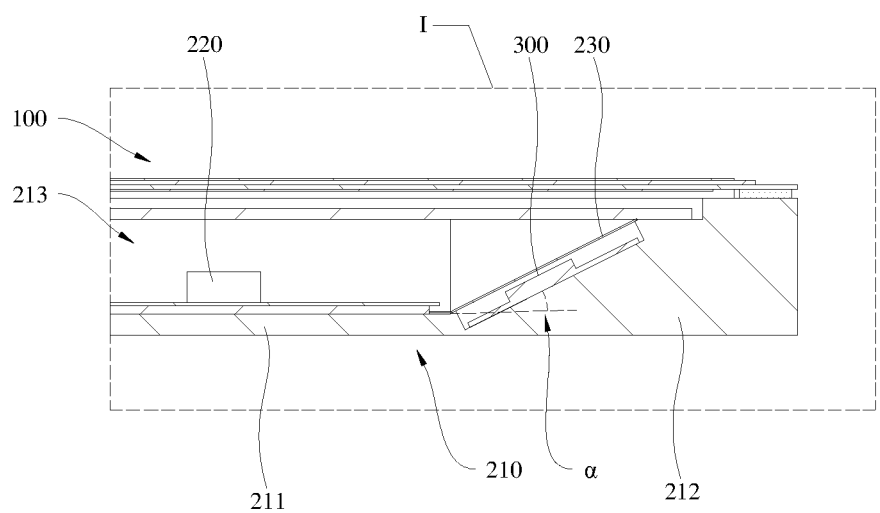
FIG. 3 is a partial enlarged schematic view at I in FIG. 2.
Figure 4:
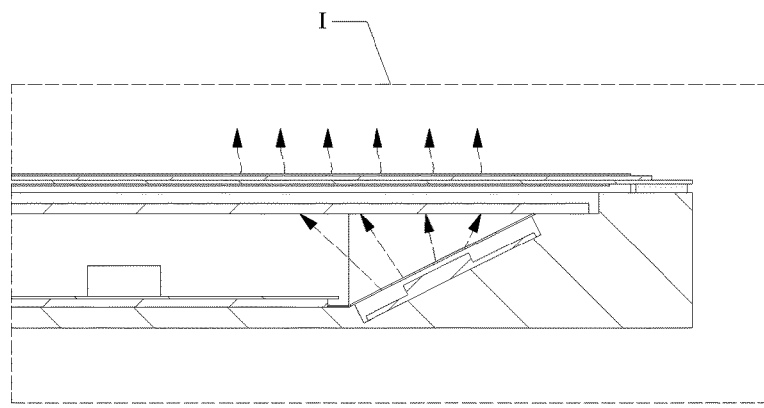
FIG. 4 is a schematic diagram illustrating a light path of ultraviolet (UV) rays emitted by a UV-ray emitting assembly in FIG. 3.

A display module 10 is provided in the present disclosure. Please refer to FIGS. 1, 2, 3, and 4 together, where FIG. 1 is a schematic structural view of a display module provided in an implementation of the present disclosure, FIG. 2 is a schematic cross-sectional view taken along line A-A in FIG. 1, FIG. 3 is a partial enlarged schematic view at I in FIG. 2, FIG. 4 is a schematic diagram illustrating a light path of ultraviolet (UV) rays emitted by a UV-ray emitting assembly in FIG. 3. In this implementation, the display module 10 includes a display panel 100 and a backlight module 200 stacked with the display panel 100. The backlight module 200 includes a back plate 210 and a light-emitting member 220, and the back plate 210 has a bottom wall 211 and multiple side walls 212. The multiple side walls 212 surrounds the bottom wall 211 to define an accommodation space 213. The light-emitting member 220 is accommodated in the accommodation space 213 and is carried on the bottom wall 211, and the light-emitting member 220 is configured to emitting visible light. The display module 10 further includes a UV-ray emitting assembly 300 accommodated in the accommodation space 213 and disposed to correspond to one of the side walls 212. The UV-ray emitting assembly 300 is obliquely disposed with respect to the display panel 100 and configured to emit UV rays to the display panel 100 so as to disinfect the display panel 100.

In this implementation, the display module 10 is applied to a display device, and is specifically applied to a display device with a touch screen, such as a ticket dispenser for train and subways, a machine control panel, a medical payment registration machine, a vehicle-mounted central control display screen, a mobile phone, a tablet computer, or the like.

In this implementation, the display module 10 emits UV rays to the display panel 100 through the UV-ray emitting assembly 300, so as to sterilize an outer surface of the display panel 100, thereby killing viruses, bacteria or the like on the outer surface of the display panel 100, achieving a self-cleaning effect on the display module 10, and further ensuring the health of the user. The UV rays emitted by the UV-ray emitting assembly 300 are electromagnetic waves with a wavelength in 270 nm~285 nm, which are invisible light and have excellent effects of disinfection and sterilization. The principle of sterilization and disinfection is that electromagnetic waves in this waveband can destroy a molecular structure of deoxyribonucleic acid (DNA) or ribonucleic acid (RNA) in microbial organism cells, resulting in growth cell death and/or regenerative cell death, achieving the effects of sterilization and disinfection. The UV-ray emitting assembly 300 is also referred to as a UV-ray light-emitting diode (LED) light bar.

Specifically, the back plate 210 has a bottom wall 211 and multiple side walls 212, the bottom wall 211 and the multiple side walls 212 cooperatively define an accommodation space 213, the UV-ray emitting assembly 300 is disposed corresponding to one of the side walls 212, and the UV-ray emitting assembly 300 is disposed obliquely with respect to the display panel 100. The UV-ray emitting assembly 300 is configured to emit UV rays to the display panel 100, so that the UV rays pass through the display panel 100, thereby disinfecting an outer surface of the display panel 100 away from the back plate 210. Because the UV-ray emitting assembly 300 is obliquely disposed with respect to the display panel 100, the UV-ray emitting assembly 300 can emit the UV rays obliquely to the display panel 100. Therefore, for the same number of UV-ray LEDs, compared with UV rays emitted directly to the display panel 100, the UV rays emitted by the UV-ray emitting assembly 300 provided in this implementation can cover a larger area, such that the UV rays emitted by the UV-ray emitting assembly 300 have a large coverage on the display panel 100, and the disinfection effect of the UV-ray emitting assembly 300 is improved. In addition, for the display panel 100 of the same size, due to the large coverage of UV rays emitted by the UV-ray emitting assembly 300 on the display panel 100, the number of the UV-ray LEDs in the UV-ray emitting assembly 300 is reduced, and cost of the UV-ray emitting assembly 300 is further reduced. In addition, the display module 10 provided in this implementation achieves the effects of self-disinfection and self-sterilization by using the principle of UV disinfection, which breaks through a conventional concept of manual spraying or manual wiping for disinfection, and can not only efficiently disinfect the display panel 100, but also has advantages of low cost, significant savings in manpower and resources, and high feasibility. In addition, the UV rays emitted by the UV-ray emitting assembly 300 can also pass through the display panel 100, so as to sterilize air around the display panel 100, thereby further ensuring the health of the user.

The UV-ray emitting assembly 300 is disposed corresponding to the side wall 212, which means that the UV-ray emitting assembly 300 is carried on the side wall 212, or the UV-ray emitting assembly 300 is disposed adjacent to the side wall 212, so that the UV-ray emitting assembly 300 is located in an edge region of the display module 10, thereby further improving the coverage of the UV rays emitted by the UV-ray emitting assembly 300 on the display panel 100.

Optionally, in an implementation, the UV-ray emitting assembly 300 is carried on an inner surface of the side wall 212 facing the accommodation space 213, and the inner surface of the side wall 212 facing the accommodation space 213 is disposed obliquely with respect to the display panel 100, so that the UV-ray emitting assembly 300 is disposed obliquely. In another implementation, the UV-ray emitting assembly 300 is obliquely disposed in the accommodation space 213, one end of the UV-ray emitting assembly 300 abuts against the bottom wall 211, and the other opposite end of the UV-ray emitting assembly 300 abuts against the side wall 212, so that the UV-ray emitting assembly 300 is obliquely disposed with respect to the display panel 100. In another implementation, the display module 10 further includes a support member for supporting the UV-ray emitting assembly 300, so that the UV-ray emitting assembly 300 is disposed obliquely with respect to the display panel 100. It can be understood that, in other implementations, the UV-ray emitting assembly 300 can be obliquely disposed relative the display panel 100 to emit UV rays obliquely to the display panel 100.

Further, the UV-ray emitting assembly 300 can also be disposed corresponding to the multiple side walls 212, so that the UV-ray emitting assembly 300 can emit UV rays obliquely in various directions to the display screen, thereby further enlarging a disinfection range of the UV-ray emitting assembly 300 for the dis play panel 100, and improving the disinfection effect.

In summary, a display module 10 is provided in the present disclosure. The display module 10 includes a display panel 100, a backlight module 200, and an UV-ray emitting assembly 300. The UV-ray emitting assembly 300 is accommodated in the accommodation space 213 of the back plate 210 of the backlight module 200 and disposed corresponding to the side wall 210 of the backlight module 200. The UV-ray emitting assembly 300 is disposed obliquely with respect to the display panel 100, so that the UV-ray emitting assembly 300 can emit UV rays obliquely to the display panel 100. Therefore, for the same number of UV-ray LEDs, compared with UV LEDs emitted directly to the display panel 100, the UV rays emitted in this implementation can cover a larger coverage area of the UV rays, so that the UV rays emitted by the UV-ray emitting assembly 300 can have a large coverage on the display panel 100, and the disinfection effect of the UV-ray emitting assembly 300 is improved. The display module 10 provided in this implementation achieves the effects of self-disinfection and self-sterilization by using the principle of UV disinfection, which breaks through a conventional concept of manual spraying or manual wiping for disinfection, and can not only efficiently disinfect the display panel 100, but also has advantages of low cost, significant savings in manpower and resources, and high feasibility. In addition, the UV rays emitted by the UV-ray emitting assembly 300 can also pass through the display panel 100, so as to sterilize the air around the display panel 100, thereby further ensuring the health of the user. Therefore, the display module 10 provided in the present disclosure disinfects the display panel 100 with the UV-ray emitting assembly 300, which has high sterilization efficiency and low costs.

Referring to FIG. 3 again, in this implementation, the UV-ray emitting assembly 300 is carried on the side wall 212, and an angle α defined between the side wall 212 and one side of the bottom wall 211 away from the accommodation space 213 satisfies 40°≤α≤70°.

In this implementation, the angle α defined between the side wall 212 and one side of the bottom wall 211 away from the accommodation space 213 satisfies 40°≤α≤70°, that is, an angle α between the light-exiting surface of the UV-ray emitting assembly 300 and the display panel 100 satisfies 40°≤α≤70°, which is beneficial to improving a coverage range of the UV rays emitted by the UV-ray emitting assembly 300 on the display panel 100. If the angle α defined between the side wall 212 and one side of the bottom wall 211 away from the accommodation space 213 is less than 40°, the UV-ray emitting assembly 300 is almost direct towards the display panel 100, and thus a transmission distance of the UV rays emitted by the UV-ray emitting assembly 300 is short, which will lead to insufficient scattering of the UV rays before reaching the display panel 100, and a reduced coverage region of the UV rays emitted by the UV-ray emitting assembly 300 on the display panel 100. If the angle α defined between the side wall 212 and one side of the bottom wall 211 away from the accommodation space 213 is greater than 70°, the UV-ray emitting assembly 300 is inclined excessively with respect to the display panel 100, so that the UV rays emitted by the UV-ray emitting assembly 300 deviates excessively from the display panel 100, more UV rays are scattered to the light-emitting member 220, and less UV rays are incident to the display panel 100, and thus the disinfection effect of the UV-ray emitting assembly 300 on the display panel 100 is weakened.

Referring to FIG. 3 again, in this implementation, the display module 10 further includes a diffuser 230, and the diffuser 230 is disposed corresponding to a light-exiting surface of the UV-ray emitting assembly 300 and is configured to diffuse the UV rays emitted by the UV-ray emitting assembly 300.

In this implementation, the diffuser 230 is disposed corresponding to the light-exiting surface of the UV-ray emitting assembly 300, which means that an orthographic projection of the diffuser 230 on the UV-ray emitting assembly 300 covers the light-exiting surface. The diffuser 230 can evenly diffuse the UV rays emitted by the UV-ray emitting assembly, thereby enlarging the coverage of the UV rays on the display panel 100, and further improving the disinfection effect of the UV-ray emitting assembly 300 on the display panel 100.

Figure 5:
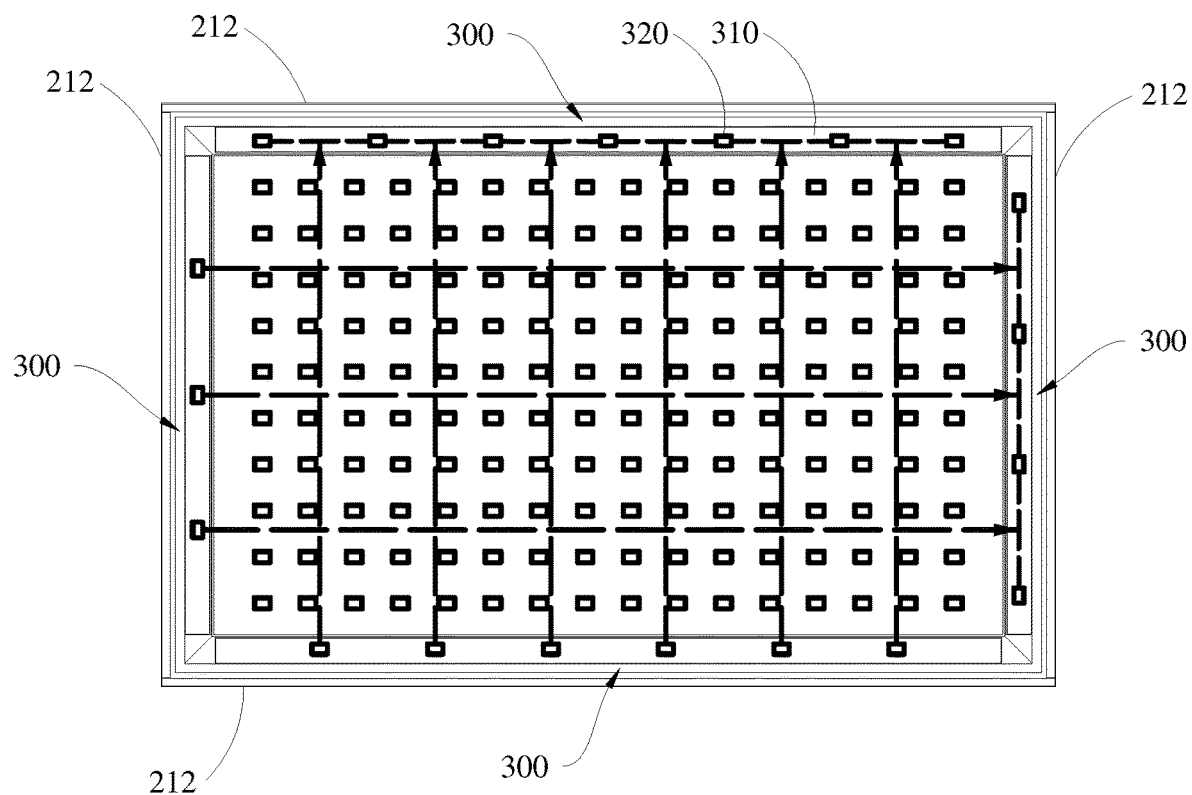
FIG. 5 is a schematic structural view of multiple UV-ray emitting members in FIG. 1 provided in one implementation.
Figure 6:
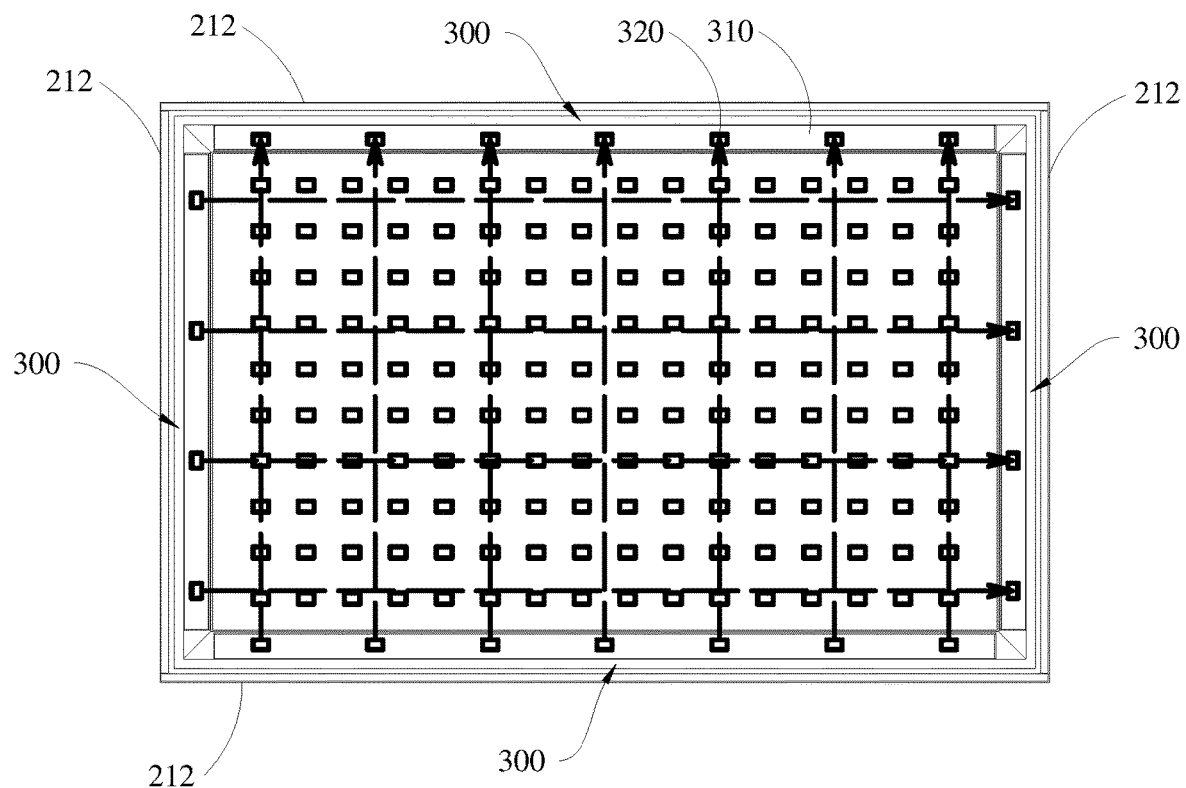
FIG. 6 is a schematic structural view of multiple UV-ray emitting members in FIG. 1 provided in another implementation.

Please refer to FIGS. 5 and 6, where FIG. 5 is a schematic structural view of multiple UV-ray emitting assemblies in FIG. 1 provided an implementation, and FIG. 6 is a schematic structural view of multiple UV-ray emitting assemblies in FIG. 1 provided another implementation. In this implementation, the display module 10 includes multiple UV-ray emitting assemblies 300, and each of the UV-ray emitting assemblies 300 is disposed correspond to one of the side walls 212. The multiple UV-ray emitting assemblies 300 each include a carrier 310 and multiple UV-ray emitting member 320, and the carrier 310 is carried on the side wall 212. The multiple UV-ray emitting member 320 are carried on the carrier 310, and the multiple UV-ray emitting member 320 are arranged at intervals. For two UV-ray emitting assemblies 300 disposed opposite to each other, in a direction from one UV-ray emitting assembly 300 to the other UV-ray emitting assembly 300, multiple UV-ray emitting members 320 in said one UV-ray emitting assembly 300 and multiple UV-ray emitting members 320 in the other UV-ray emitting assembly 300 are staggered with one another or directly opposite to one another.

In this implementation, each of the UV-ray emitting assemblies 300 is disposed corresponding to one of the side walls 212, so that the UV rays is emitted obliquely upward from a periphery of the back plate 210 to the display panel 100, thereby further improving the coverage of the UV rays on the display panel 100, and further improving the disinfection effect of the UV-ray emitting assemblies 300 on the display panel 100. The UV-ray emitting member 320 is also referred to as an UV-ray LED lamp bead.

Specifically, in one implementation, referring to FIG. 5, a dotted line with an arrow in FIG. 5 is used to illustrate a projection. For the two UV-ray emitting assemblies 300 disposed opposite to each other, in the direction from one UV-ray emitting assembly 300 to the other UV-ray emitting assembly 300, the multiple UV-ray emitting members 320 of said one UV-ray emitting assembly 300 and the multiple UV-ray emitting members 320 of the other UV-ray emitting assembly 300 are disposed in a staggered manner, to reduce an overlapping range of the UV rays emitted by the multiple UV-ray emitting member 320 on the display panel 100, such that a smaller number of UV-ray emitting members 320 need to be disposed when the UV rays covers the whole display panel 100, thereby reducing the cost. It should be noted that the multiple UV-ray emitting members 320 of one UV-ray emitting assembly 300 and the multiple UV-ray emitting members 320 of the other UV-ray emitting assembly 300 are staggered with one another, which means that for two UV-ray emitting assemblies 300 opposite to each other, in the direction from one UV-ray emitting assembly 300 to the other UV-ray emitting assembly 300, orthographic projections of the UV-ray emitting members 320 of one UV-ray emitting assembly 300 on the other UV-ray emitting assembly 300 falls between two adjacent UV-ray emitting members 320, and the orthographic projections of the UV-ray emitting members 320 of one UV-ray emitting assembly 300 on the other UV-ray emitting assembly 300 is in the same arrangement direction as the multiple UV-ray emitting members 320 of the other UV-ray emitting assembly 300, i.e., on the same line, or approximately on the same line.

In another implementation, referring to FIG. 6, a dotted line with an arrow in FIG. 6 is used to illustrate a projection. For two UV-ray emitting assemblies 300 opposite to each other, in a direction from one UV-ray emitting assembly 300 to the other UV-ray emitting assembly 300, the multiple UV-ray emitting members 320 of one UV-ray emitting assembly 300 and the multiple UV-ray emitting members 320 of the other UV-ray emitting assembly 300 are directly opposite to one another, so as to increase an overlapping range of the UV rays on the display panel 100, and increase an irradiation amount of the UV rays on the display panel 100, thereby improving the disinfection effect on the display panel 100. It should be noted that, the multiple UV-ray emitting members 320 of one UV-ray emitting assembly 300 and the multiple UV-ray emitting members 320 of the other UV-ray emitting assembly 300 are directly opposite to one another, which means that for two UV-ray emitting assemblies 300 opposite to each other, in the direction from one UV-ray emitting assembly 300 to the other UV-ray emitting assembly 300, orthographic projections of UV-ray emitting members 320 of one UV-ray emitting assembly 300 on the other UV-ray emitting assembly 300 falls into the UV-ray emitting members 320 of the other UV-ray emitting assembly 300, and the orthographic projections of UV-ray emitting members 320 of one UV-ray emitting assembly 300 on the other UV-ray emitting assembly 300 and the UV-ray emitting members 320 of the other UV-ray emitting assembly 300 overlap or approximately overlap.

Figure 7:
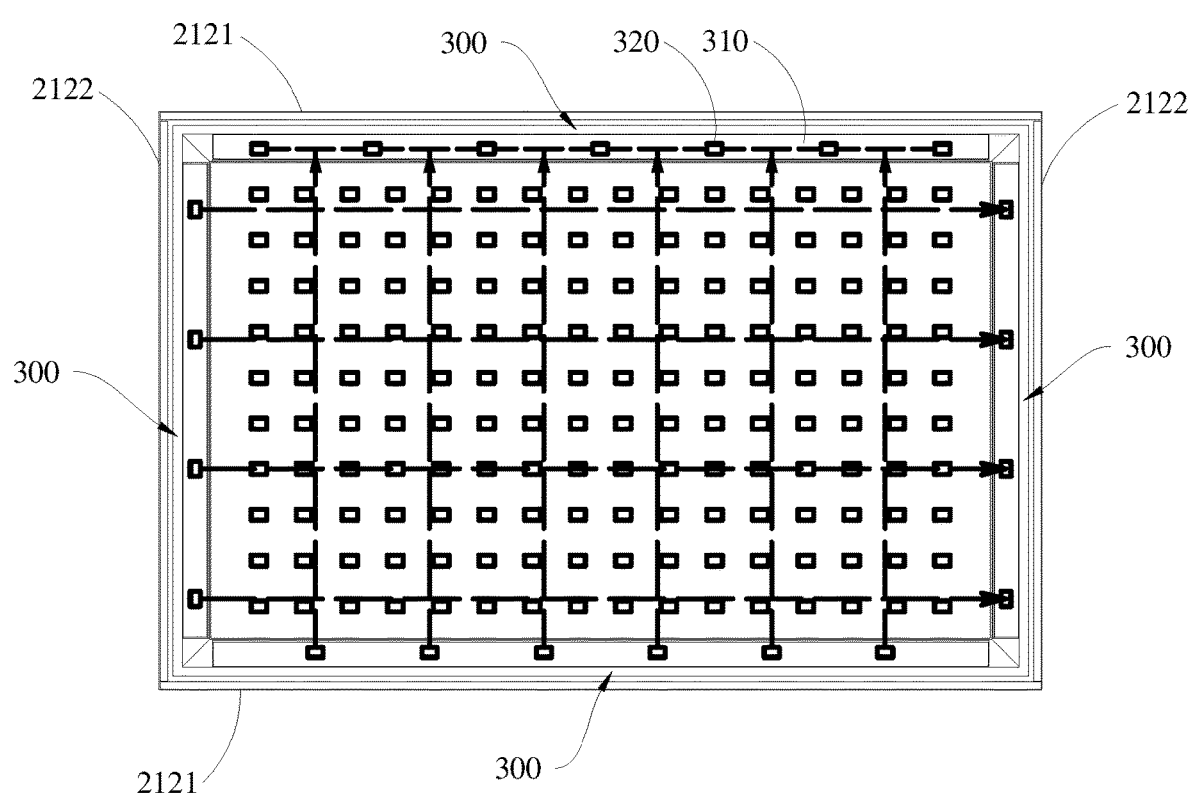
FIG. 7 is a schematic structural view of multiple UV-ray emitting members in FIG. 1 provided in another implementation.

Please refer to FIG. 7, where FIG. 7 is a schematic structural view of multiple UV-ray emitting members in FIG. 1 provided in another implementation. In this implementation, the multiple side walls 212 includes two long walls 2121 opposite to each other and two short walls 2122 opposite to each other. The length of each of the two long walls 2121 is greater than that of each of the two short walls 2122, and each of the two long walls 2121 is connected to one of the two short walls 2122 in a bending manner. For two UV-ray emitting assemblies 300 disposed on the two long walls 2121, in a direction from one UV-ray emitting assembly 300 to the other UV-ray emitting assembly 300, multiple UV-ray emitting members 320 in one UV-ray emitting assembly 300 and multiple UV-ray emitting assemblies 300 in the other UV-ray emitting assembly 300 are staggered (i.e., interlaced) with one another. For two UV-ray emitting assemblies 300 disposed on the two short walls 2122, in a direction from one UV-ray emitting assembly 300 to the other UV-ray emitting assembly 300, the multiple UV-ray emitting members 320 in one UV-ray emitting assembly 300 and the multiple UV-ray emitting members 320 in the other UV-ray emitting assembly 300 are directly opposite to one another.

In this implementation, a dotted line with an arrow in FIG. 7 is used to illustrate a projection. Because a distance for transmitting the UV rays emitted by the two UV-ray emitting assemblies 300 disposed on the two long walls 2121 is short, the UV-ray emitting members 320 of said two UV-ray emitting assemblies 300 are staggered with one another to reduce an overlapping range of the UV rays emitted by the multiple UV-ray emitting members 320 on the display panel 100. Therefore, a smaller number of UV-ray emitting members 320 need to be disposed when the UV rays covers the whole display panel 100, and thus the cost is reduced. Because a distance for transmitting the UV rays emitted by the two UV-ray emitting assemblies 300 disposed on the two short walls 2122 is relatively long, the UV-ray emitting members 320 of the two UV-ray emitting assemblies 300 disposed on the two short walls 2122 are arranged to directly opposite to one other, so as to improve a coverage region of the UV rays on the display panel 100, thereby allowing the UV rays to be distributed more evenly on the display panel 100, and further improving the disinfection effect on the display panel 100. The UV-ray emitting members 320 being staggered with one another or directly opposite to one another has been described in the above implementations, and will not be elaborated herein.

In addition, referring to FIG. 3 and FIG. 6 again, the light-emitting unit 220 includes a carrier portion and multiple light-emitting portions, and the multiple light-emitting portions are arranged at intervals on the carrier portion and face the display panel 100. The backlight module 200 further includes a light-reflective layer disposed on a surface of the carrier portion carrying the multiple light-emitting portions and disposed to avoid the multiple light-emitting portions. The light-reflective layer is configured to emit the UV rays emitted by the UV-ray emitting assembly 300 to the display panel 100, so as to reduce loss of the UV rays, thereby assisting irradiation of the UV rays to the display panel 100, and further improving the disinfection effect on the display panel 100.

Optionally, the display module 10 further includes an adhesive frame used for bonding the display panel 100 and the back plate 210. The adhesive frame is a foam adhesive frame, so that the adhesive frame provides an elastic buffer while bonding the display panel 100 and the back plate 210, and can play a buffering role when the display module 10 is impacted by the outside.

Optionally, the back plate 210 has a first surface, a second surface and a third surface which are connected sequentially in bending manner, the first surface and the third surface are in parallel, and the first surface and the third surface are disposed to face the display panel 100. The first surface is configured to carry the adhesive frame. The backlight module 200 further includes an optical film, the optical film is carried on the third surface, and the third surface supports the optical film, and the second surface supports the optical film. The optical film is configured to scatter and equalize the UV rays emitted by the UV-ray emitting assembly 300, so as to improve the coverage and uniformity of the UV rays emitted to the display panel 100, thereby improving the disinfection effect on the display panel 100.

Further, in a direction from the light-emitting member 220 to the display panel 100, a distance between the first surface and the third surface is in 1 mm~2 mm, which facilitates the optical film to diffuse the UV rays emitted by the UV-ray emitter 320, and facilitates the diffusion of the visible light emitted by the light-emitting portion. For example, the distance between the first face and the third face may be, but is not limited to, 1 mm, 1.2 mm, 1.4 mm, 1.6 mm, 1.8 mm, 2 mm, or any other arbitrary value between 1 mm and 2 mm. If the distance between the first surface and the third surface is less than 1 mm, the UV rays and the visible light are emitted to the display panel 100 without being diffused after being subjected to light equalization by the optical film, so that the coverage of the UV rays and the visible light on the display panel 100 is reduced, which neither contributes to sterilization of the display panel 100, nor contributes to the display effect of the display panel 100. If the distance between the first surface and the third surface is greater than 2 mm, the display module 10 will be too thick, which is not beneficial to light and thin design of the display module 10. Therefore, in the direction from the light-emitting member 220 to the display panel 100, the distance between the first surface and the third surface is in 1 mm~2 mm, which facilitates the optical film to diffuse the UV rays emitted by the UV-ray emitting member 320, and facilitates to diffuse the visible light emitted by the light-emitting member.

Optionally, the light-emitting portion may be, but not limited to, an LED, a mini LED, or a micro LED.

Further, the optical film abuts against a diffusion plate at a surface of the optical film away from the display panel 100, so that a distance for the UV rays to be emitted to the optical film after passing through the diffusion plate is reduced, and the diffusion effect of the UV rays is further improved.

In this implementation, the UV-ray emitting assembly 300 is fast and efficient in disinfecting the display panel 100, and specifically, the UV-ray emitting assembly 300 only needs 10 minutes to 20 minutes to complete disinfection of the display panel 100. For example, the UV-ray emitting assembly 300 only needs 10 min, 12 min, 15 min, 18 min, 20 min, or other value between 10 min and 20 min to complete the disinfection of the display panel 100.

Figure 8:
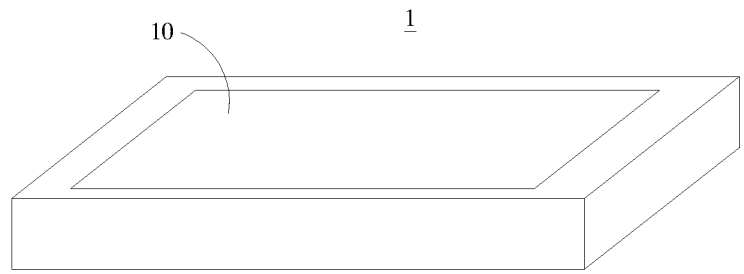
FIG. 8 is a schematic structural vies of an electronic device provided in an implementation of the present disclosure.
Figure 9:
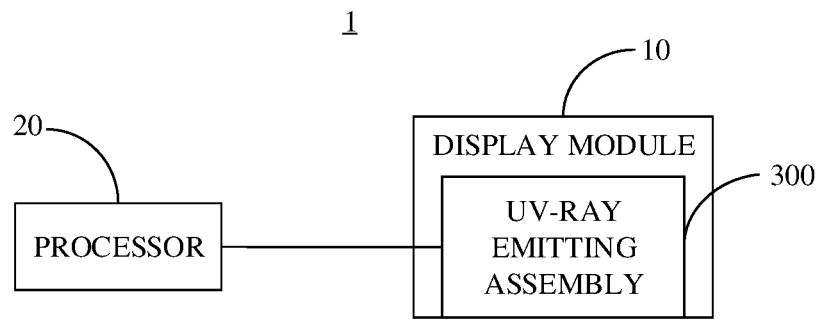
FIG. 9 is a block diagram illustrating electrical connections in the electronic device in FIG. 8.

An electronic device 1 is further provided in the present disclosure. Please refer to FIG. 8 and FIG. 9, where FIG. 8 is a schematic structural view of an electronic device provided in an implementation of the present disclosure, and FIG. 9 is a block diagram illustrating electrical connections in the electronic device in FIG. 8. In this implementation, the electronic device 1 includes a processor 20 and the display module 10 in any one of the foregoing implementations. The processor 20 is electrically connected to the UV-ray emitting assembly 300 in the display module 10 and controls the UV-ray emitting assembly 300.

In this implementation, the electronic device 1 is a display device having a touch screen. For example, the electronic device 1 may be, but is not limited to, a ticket dispenser for train and subways, a machine control panel, a medical payment registration machine, a vehicle-mounted central control display screen, a mobile phone, a tablet computer, or the like.

In this implementation, the electronic device 1, the electronic device 1 can control, through the processor 20, the UV-ray emitting assembly 300 in the display module 10 to emit UV rays to disinfect the display panel 100 of the display module 10, and the disinfection effect is efficient.

Figure 10:
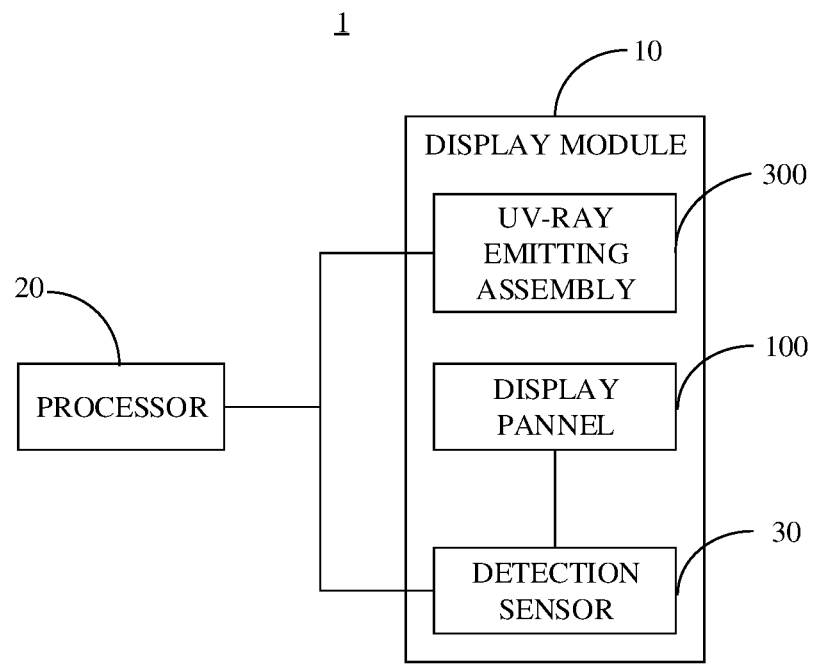
FIG. 10 is a block diagram illustrating an electrical connection between a processor and a detection sensor in FIG. 8.

Please refer to FIG. 10, where FIG. 10 is a block diagram illustrating an electrical connection between a processor and a detection sensor in FIG. 8. In this implementation, the display module 10 further includes a detection sensor 30 electrically connected to the display panel 100 for detecting whether the display panel 100 is touched. The processor 20 is electrically connected to the detection sensor 30, and is configured to record the number of times that the display panel 100 is touched and obtain a first number of times of detection, and compare of the first number of times of detection and the first preset number of times. When the processor 20 determines that the first number of times of detection is greater than or equal to the first preset number of times, the processor 20 controls the UV-ray emitting assembly 300 to emit UV rays.

In this implementation, the detection sensor 30 detects whether or not the display panel 100 is touched, and records and obtains the first number of times of detection by the processor 20. An accumulated level of bacteria, viruses and the like on the surface of the display panel 100 after being touched by the user can be deduced from the first number of times of detection. When the processor 20 determines that the first number of times of detection is greater than or equal to the first preset number of times, which means bacteria, viruses and the like accumulated on the surface of the display panel 100 reach a degree that cleaning and disinfection are required, the processor 20 controls the UV-ray emitting assembly 300 to emit UV rays to disinfect the display panel 100, such that the display panel 100 is cleaned to prevent bacteria, viruses and the like on the display panel 100 from damaging the health of the user. The first preset number of times may be set according to an actual application condition, which is not limited herein.

Optionally, the detection sensor 30 may be, but not limited to, a pressure sensor, and the pressure sensor detects whether the display panel 100 is touched by detecting a pressure generated when a user touches the display panel 100. Alternatively, the detection sensor 30 may be an optical sensor, and the optical sensor detects whether the display panel 100 is touched by detecting a distance between a user's finger and the display panel 100. Alternatively, the detection sensor 30 may be a temperature sensor, and the temperature sensor detects whether the display panel 100 is touched by detecting a temperature change on the display panel 100.

Figure 11:
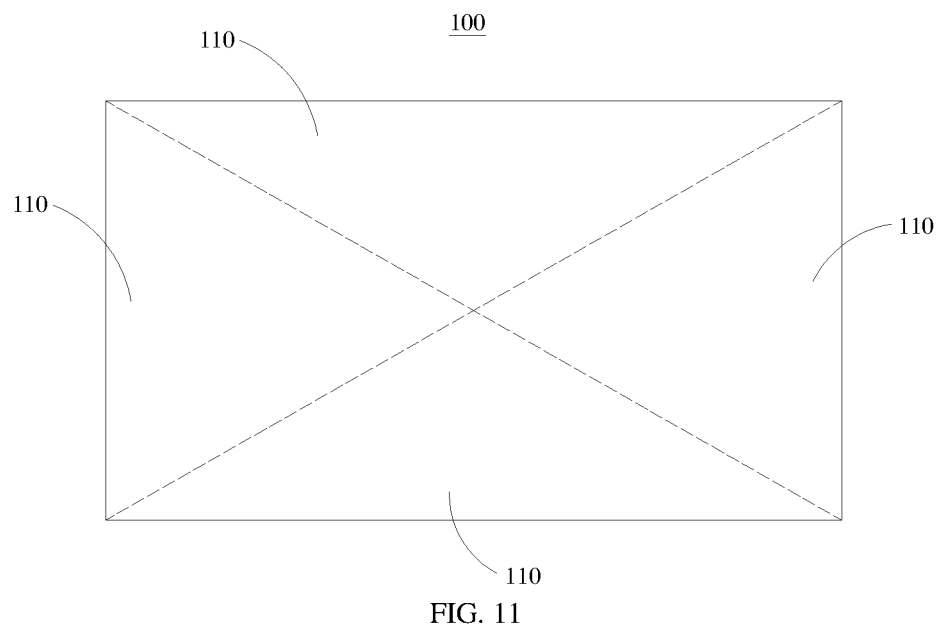
FIG. 11 is a schematic diagram illustrating a partition of a display panel provided in an implementation of the present disclosure.
Figure 12:
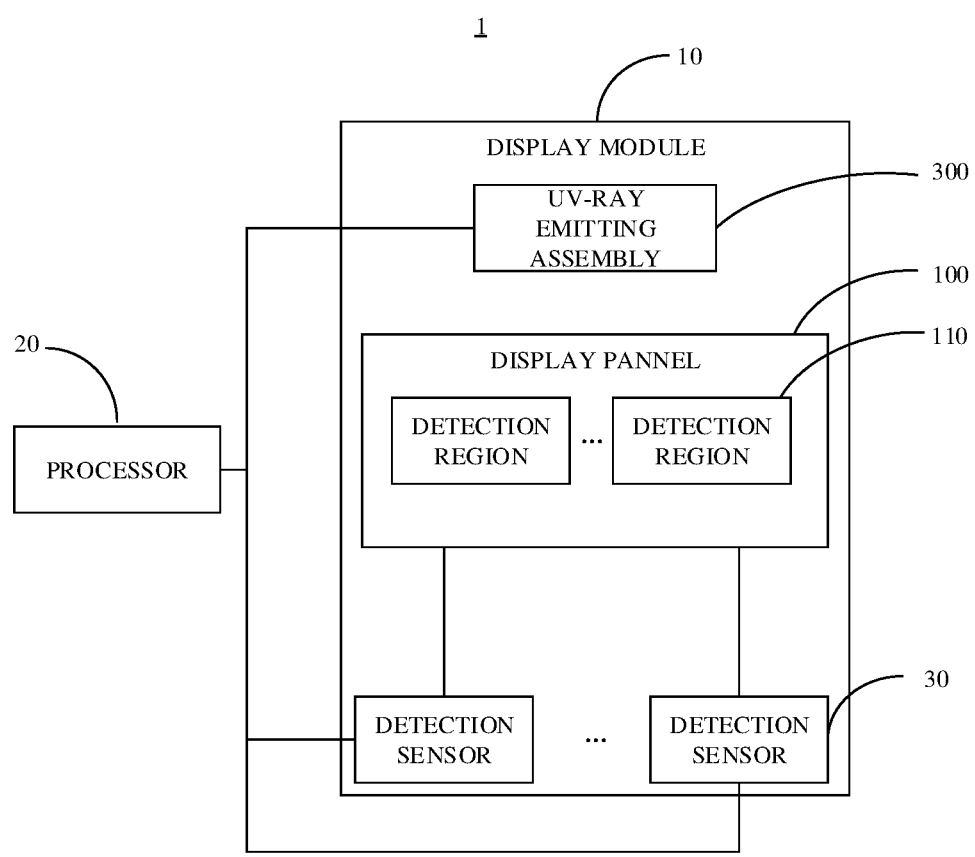
FIG. 12 is a block diagram illustrating an electrical connection between a processor and a detection sensor in FIG. 11.

Please refer to FIG. 6, FIG. 11, and FIG. 12, where FIG. 11 is a schematic diagram illustrating a partition of a display panel provided in an implementation of the present disclosure, and FIG. 12 is a block diagram illustrating an electrical connection between a processor and a detection sensor in FIG. 11. In this implementation, the display module 10 includes multiple UV-ray emitting assemblies 300. The display panel 100 includes multiple detection regions 110. The multiple UV-ray emitting assemblies 300 each is disposed corresponding to one of the detection regions 110. The display module 10 includes multiple detection sensor 30s. The multiple detection sensor 30s are electrically connected to the display panel 100, each of the detection sensor 30s is configured to detect whether one of the detection regions 110 is touched, different detection sensor 30s are configured to detect whether one of the detection regions 110 is touched, and different detection sensor 30s are configured to detect different regions. The processor 20 is electrically connected to the multiple detection sensor 30s and is configured to record the number of times each of the detection regions 110 is touched and obtain multiple second numbers of times of detection. The processor 20 is configured to determine a detection region 110, the second number of times of detection of which is greater than or equal to the second preset number of times, as a region to-be-disinfected. When the processor 20 determines at least one of the multiple detection regions 110 as the region to-be-disinfected, the processor 20 is configured to control the UV-ray emitting assembly 300 disposed corresponding to the region to-be-disinfected to emit UV rays.

In this implementation, the detection region 110 is a virtually divided region, so that the detection sensor 30 performs corresponding detection and the UV-ray emitting assembly 300 performs corresponding disinfection. It can be understood that the detection region 110 is not physically divided, that is, the display panel 100 is an integrated structure.

In this implementation, the detection sensor 30 detects whether or not a detection region 110 on the display panel 100 is touched, and records and obtains the second number of times of detection by the processor 20. The accumulated level of bacteria, viruses and the like on the surface of the display panel 100 after the detection region 110 is touched by the user can be deduced from the second number of times of detection. When the processor 20 determines that the second number of times of detection is greater than or equal to the second preset number of times, which means that, bacteria, viruses and the like accumulated on the surface of the display panel 100 in the detection region 110 reach a degree that cleaning and disinfection are required, the processor 20 determines the detection region 110 as a region to-be-disinfected, and the processor 20 controls the UV-ray emitting assembly 300 corresponding to the region to-be-disinfected to UV rays so as to disinfect the display panel 100 in the detection region 110. In this way, the display panel 100 is cleaned to prevent bacteria, viruses and the like on the display panel 100 from damaging the health of the user. The second preset number of times may be set according to an actual application condition, which is not limited herein.

In this implementation, the display panel 100 is divided into multiple detection regions 110, so as to perform detection respectively and clean and disinfect independently, thereby realizing accurate detection and disinfection on each detection region 110 of the display panel 100, and avoiding unnecessary disinfection on a region which does not need disinfection, thereby improving disinfection efficiency and reducing disinfection costs.

In this implementation, multiple detection regions 110 are connected, and two adjacent detection regions 110 do not have an overlapping region, thereby facilitating the detection of the detection regions 110 by the sensor. A partition of the display panel 100 illustrated in FIG. 11 are merely illustrative, and it should be understood that each of the detection regions 110 may be correspondingly close to one UV-ray emitting assembly 300, and different detection regions 110 may be correspondingly close to different UV-ray emitting assemblies 300.

In other implementations, there is an overlapping region between different detection regions 110, wherein each of the detection regions 110 is correspondingly a region on the display panel 100 covered by the UV rays emitted by the UV-ray emitting assembly 300. Since it is difficult for the UV rays emitted by the multiple UV-ray emitting assembly 300 to have no overlapping region on the display panel 100. Therefore, there is an overlapping region between different detection regions 110, which helps to disinfect the display panel 100 by using the UV-ray emitting assembly 300 to the maximum extent.

Please further refer to FIG. 10, and in this implementation, the display module 10 further includes the detection sensor 30 electrically connected to the display panel 100 for detecting whether the display panel 100 is touched. The processor 20 is electrically connected to the detection sensor 30 and is configured to record the number of times that the display panel 100 is touched and obtain a third number of times of detection. The processor 20 is configured to count the third numbers of times of detection in each time period in a historical preset number of days to obtain a first time period and a second time period. The first time period is a time period in which the third number of times of detection is less than or equal to a preset threshold. The second time period is a time period in which the third number of times of detection is greater than the preset threshold. When the processor 20 determines that the current moment is in the first time period and the display panel 100 is not touched currently, the processor 20 controls the UV-ray emitting assembly 300 to be turned on. When the processor 20 determines that the current moment is in the second time period, the processor 20 controls the UV-ray emitting assembly 300 to be turned off or kept in a turned-off state. The preset threshold may be set according to an actual application, which is not limited herein.

In this implementation, the processor 20 is configured to count the third numbers of times of detection in each time period in a historical preset number of days to obtain the first time period and the second time period. The first time period is a time period in which the user uses the electronic device 1 (namely, the user touches the display panel 100) less frequently, the second time period is a time period in which the user uses the electronic device 1 more frequently. The first time period and the second time period together form one day. It may be appreciated that a day may include multiple first time periods and multiple second time periods.

In this implementation, by making statistics of the first time period and the second time period, the processor 20 can control the UV-ray emitting assembly 300 to achieve full-automatic intelligent cleaning and disinfection, thereby improving the disinfection efficiency for the display panel 100 and effectively avoiding the user.

Alternatively, the historical preset number of days may be, but is not limited to, one week, one month, one quarterly, or the like.

Further, the processor 20 regularly updates the first time period and the second time period, so as to deal with different situations in which the electronic device 1 is used in different periods, and further optimize the disinfection of the display panel 100 by the UV-ray emitting assembly 300. Optionally, the periodic updating can be carried out by the processor 20 at intervals which may be, but is not limited to, one month, one quarter, one year, or the like.

Further, when the processor 20 controls the UV-ray emitting assembly 300 to operate, the processor 20 is further configured to control the light-emitting member 220 and the display panel 100 to operate, to make the light-emitting member 220 emit visible light to the display panel 100 so as to display a prompt on the display panel 100. The prompt is used to prompt the user to move away from the electronic device 1, thereby preventing UV rays emitted by the UV-ray emitting assembly 300 from damaging the health of the user. For example, the prompt may be "in UV disinfection, do not approach", or "dangerous, do not approach", so long as the prompt can serve as a warning.

Therefore, the electronic device 1 provided in the present disclosure not only can control the UV-ray emitting assembly 300 in the display module 10 to emit UV rays so as to disinfect the display panel 100 of the display module 10, but also warn the user to keep away when the UV-ray emitting assembly 300 is operating, so as to avoid damage to the health of the user.

Further, when the UV-ray emitting assembly 300 is operating, the processor 20 is further configured to control the prompt to move on the display panel 100, so as to prevent an afterimage from being formed on the display panel 100.

Optionally, the processor 20 may, but is not limited to, control the prompt to vertically roll, horizontally roll, or obliquely roll on the display panel 100, as long as the prompt can move on the display panel 100.

Further, when the UV-ray emitting assembly 300 is operating and the detection sensor 30 30 detects that the display panel 100 is touched, the processor 20 controls the UV-ray emitting assembly 300 to stop operation, so as to prevent the damage to the health of the user by the ultraviolet rays.

Figure 13:
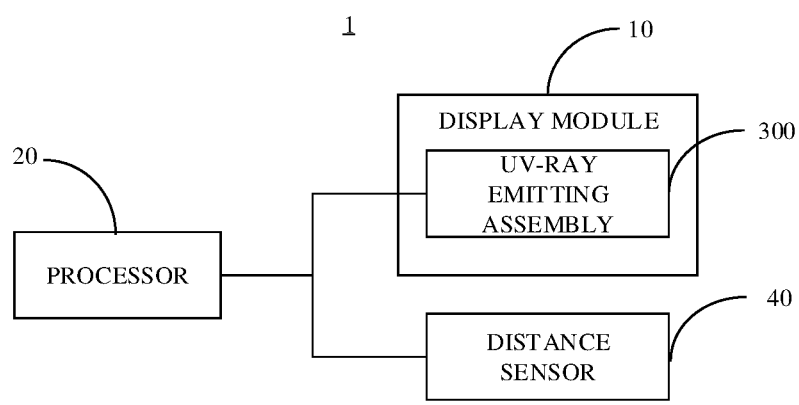
FIG. 13 is a block diagram illustrating an electrical connection between a processor and a distance sensor in FIG. 8.

Please further refer to FIG. 13, FIG. 13 is a block diagram illustrating an electrical connection between a processor and a distance sensor in FIG. 8. In this implementation, the electronic device 1 further includes a distance sensor 40, and the distance sensor 40 is configured to detect a current distance between a living body outside the display module 10 and the display module 10. The processor 20 is electrically connected to the distance sensor 40, and is configured to receive the current distance and compare the current distance with the preset distance. When the UV-ray emitting assembly 300 is emitting UV rays to disinfect the display panel 100 and the processor 20 determines that the current distance is less than or equal to the predetermined distance, the processor 20 is configured to control the UV-ray emitting assembly 300 to stop emitting UV rays.

In this implementation, when the UV-ray emitting assembly 300 is emitting UV rays to disinfect the display panel 100, the distance sensor 40 detects the current distance between the living body outside the display module 10 and the display module 10, where the living body refers to the user.

When the UV-ray emitting assembly 300 is emitting UV rays to disinfect the display panel 100, and the processor 20 determines that the current distance is less than or equal to the preset distance, the processor 20 is configured to control the UV-ray emitting assembly 300 to stop emitting UV rays, so as to prevent the UV rays from irradiating the user to damage the health of the user. When the processor 20 determines that the current distance is greater than the predetermined distance, the processor 20 controls the UV-ray emitting assembly 300 to restart, so as to continue to disinfect the display panel 100. The preset distance is set according to an actual situation, which is not limited herein. For example, greater power of the UV-ray emitting assembly 300 will lead to greater preset distance.

Further, a first preset distance and a second preset distance are set, where the first preset distance is greater than the second preset distance. When the processor 20 determines that the current distance is less than or equal to the first preset distance, the processor 20 determines whether the living body has a moving tendency towards the display module 10, that is, calculates a change rate at which the current distance is close to the second preset distance, so as to calculate a moving acceleration of the living body towards the display module 10, and compares the moving acceleration with a preset moving acceleration. When the processor 20 determines that the moving acceleration is greater than or equal to the preset moving acceleration, or when the processor 20 determines that the current distance is less than or equal to the second preset distance, the processor 20 controls the UV-ray emitting assembly 300 to stop emitting UV rays. The first preset distance is set, to prevent a situation where the living body moves toward the display module 10 too fast for the processor 20 to control the UV-ray emitting assembly 300 to stop emission of UV rays in time.

Although the implementations of the present disclosure have been shown and described, it should be understood that the above implementations are illustrative and cannot be construed as limitations to the present disclosure. Those skilled in the art can make changes, modifications, replacements, and variations to the above implementations within the scope of the present disclosure, and these changes and modifications shall also belong to the scope of protection of the present disclosure.

What is claimed is:

1. A display module comprising a display panel and a backlight module stacked with the display panel, wherein the backlight module comprises:
   a back plate having a bottom wall and a plurality of side walls, wherein the plurality of side walls surround the bottom wall to define an accommodation space; and
   a light-emitting member accommodated in the accommodation space and carried on the bottom wall, wherein the light-emitting member is configured to emit visible light;
   wherein the display module further comprises:
   an ultraviolet (UV)-ray emitting assembly accommodated in the accommodation space and disposed-on one of the plurality of side walls, wherein the UV-ray emitting assembly is obliquely disposed with respect to the display panel and configured to emit UV rays from a side located within the accommodation space and away from a display surface of the display panel to the display panel so that the UV rays pass through the display panel and disinfect the display surface of the display panel and air at a side of the display surface of the display panel.

2. The display module of claim 1, wherein the UV-ray emitting assembly is carried on the one of the plurality of side walls, and an angle $\alpha$ defined between the one of the plurality of side walls and one side of the bottom wall away from the accommodation space satisfies: $40° \leq \alpha \leq 70°$.

3. The display module of claim 1, further comprising:
   a diffuser disposed corresponding to a light-exiting surface of the UV-ray emitting assembly and configured to diffuse the UV rays emitted by the UV-ray emitting assembly.

4. The display module of claim 3, wherein an orthographic projection of the diffuser on the UV-ray emitting assembly covers the light-exiting surface of the UV-ray emitting assembly.

5. The display module of claim 1, wherein the UV-ray emitting assembly is implemented as a plurality of UV-ray emitting assemblies, each of the plurality of UV-ray emitting assemblies is disposed on one of the plurality of side walls; and wherein each of the plurality of UV-ray emitting assemblies comprises:
   a carrier carried on a side wall; and
   a plurality of UV-ray emitting members carried on the carrier and arranged at intervals; wherein
   for two UV-ray emitting assemblies disposed opposite to each other, in a direction from one UV-ray emitting assembly to the other UV-ray emitting assembly, a plurality of UV-ray emitting members in said one UV-ray emitting assembly and a plurality of UV-ray emitting members in the other UV-ray emitting assembly are staggered with one another.

6. The display module of claim 1, wherein the UV-ray emitting assembly is implemented as a plurality of UV-ray emitting assemblies, each of the plurality of UV-ray emitting assemblies is disposed on one of the plurality of side walls; and wherein each of the plurality of UV-ray emitting assemblies comprises:
   a carrier carried on a side wall; and
   a plurality of UV-ray emitting members carried on the carrier and arranged at intervals; wherein for two UV-ray emitting assemblies disposed opposite to each other, in a direction from one UV-ray emitting assembly to the other UV-ray emitting assembly, a plurality of UV-ray emitting members in said one UV-ray emitting assembly and a plurality of UV-ray emitting members in the other UV-ray emitting assembly are directly opposite to one another.

7. An electronic device, wherein the electronic device comprises a processor and a display module, wherein the display module includes a display panel and a backlight module stacked with the display panel, and the backlight module comprises:
a back plate having a bottom wall and a plurality of side walls, wherein the plurality of side walls surround the bottom wall to define an accommodation space; and
a light-emitting member accommodated in the accommodation space and carried on the bottom wall, wherein the light-emitting member is configured to emit visible light;
wherein the display module further comprises:
an ultraviolet (UV)-ray emitting assembly accommodated in the accommodation space and disposed on one of the plurality of side walls, wherein the UV-ray emitting assembly is obliquely disposed with respect to the display panel and configured to emit UV rays from a side located within the accommodation space and away from a display surface of the display panel to the display panel so that the UV rays pass through the display panel and disinfect the display surface of the display panel and air at a side of the display surface of the display panel; wherein,
the processor is electrically connected to the ultraviolet (UV)-ray emitting assembly and is configured to control the UV-ray emitting assembly.

8. The electronic device of claim 7, wherein the UV-ray emitting assembly is carried on the one of the plurality of side walls, and an angle α defined between the one of the plurality of side walls and one side of the bottom wall away from the accommodation space satisfies: $40°≤α≤70°$.

9. The electronic device of claim 8, further comprising:
a diffuser disposed corresponding to a light-exiting surface of the UV-ray emitting assembly and configured to diffuse the UV rays emitted by the UV-ray emitting assembly.

10. The electronic device of claim 9, wherein an orthographic projection of the diffuser on the UV-ray emitting assembly covers the light-exiting surface of the UV-ray emitting assembly.

11. The electronic device of claim 7, wherein the UV-ray emitting assembly is implemented as a plurality of UV-ray emitting assemblies, each of the plurality of UV-ray emitting assemblies is disposed on one of the plurality of side walls; and wherein each of the plurality of UV-ray emitting assemblies comprises:
a carrier carried on a side wall; and
a plurality of UV-ray emitting members carried on the carrier and arranged at intervals; wherein
for two UV-ray emitting assemblies disposed opposite to each other, in a direction from one UV-ray emitting assembly to the other UV-ray emitting assembly, a plurality of UV-ray emitting members in said one UV-ray emitting assembly and a plurality of UV-ray emitting members in the other UV-ray emitting assembly are staggered with one another.

12. The electronic device of claim 7, wherein the UV-ray emitting assembly is implemented as a plurality of UV-ray emitting assemblies, each of the plurality of UV-ray emitting assemblies is disposed on one of the plurality of side walls; and wherein each of the plurality of UV-ray emitting assemblies comprises:
a carrier carried on a side wall; and
a plurality of UV-ray emitting members carried on the carrier and arranged at intervals; wherein
for two UV-ray emitting assemblies disposed opposite to each other, in a direction from one UV-ray emitting assembly to the other UV-ray emitting assembly, a plurality of UV-ray emitting members in said one UV-ray emitting assembly and a plurality of UV-ray emitting members in the other UV-ray emitting assembly are directly opposite to one another.

13. The electronic device of claim 7, wherein the display module further comprises:
a detection sensor electrically connected to the display panel and configured to detect whether or not the display panel is touched; wherein,
the processor is electrically connected to the detection sensor, and is configured to record the number of times the display panel is touched to obtain a first number of times of detection, and compare the first number of times of detection with a first preset number of times; and
the processor is configured to control the UV-ray emitting assembly to emit UV rays when the processor determines that the first number of times of detection is greater than or equal to the first preset number of times.

14. The electronic device of claim 13, wherein the UV-ray emitting assembly is implemented as a plurality of UV-ray emitting assemblies, the display panel has a plurality of detection regions, and each of the plurality of UV-ray emitting assemblies is disposed on one of the plurality of detection regions;
the detection sensor is implemented as a plurality of detection sensors, the plurality of detection sensors are electrically connected to the display panel, each of the plurality of detection sensors is configured to detect whether one of the detection regions is touched, and different detection sensors are configured to detect different detection regions; and
the processor is electrically connected to the plurality of detection sensors and is configured to respectively record the number of times each of the plurality of detection regions is touched and obtain a plurality of second numbers of times of detection, the processor is configured to determine a detection region in which a second number of times of detection is greater than or equal to a second preset number of times as a region to-be-disinfected, and the processor is configured to control the UV-ray emitting assembly disposed on the region to-be-disinfected to emit UV rays when the processor determines that at least one of the plurality of detection regions is the region to-be-disinfected.

15. The electronic device of claim 7, wherein the display module further comprises:
a detection sensor electrically connected to the display panel and configured to detect whether or not the display panel is touched; wherein,
the processor is electrically connected to the detection sensor and configured to record the number of times that the display panel is touched to obtain a third number of times of detection, the processor is configured to count the third number of times of detection in each time period in a historical preset number of days, to obtain a first time period and a second time period, wherein the first time period is a time period in which the third number of times of detection is less than or equal to a preset threshold, the second time period is a time period in which the third number of times of detection is greater than the preset threshold;

the processor is configured to turn on the UV-ray emitting assembly, when the processor determines that a current moment is in the first time period and the display panel is not touched currently; and the processor is configured to turn off the UV-ray emitting assembly or keep the UV-ray emitting assembly in a turn-off state, when the processor determines that the current moment is in the second time period.

16. The electronic device of claim 7, further comprising:

a distance sensor configured to detect a current distance between the display module and a living body outside the display module; wherein, the processor is electrically connected to the distance sensor and is configured to receive the current distance and compare the current distance with a preset distance; and the processor is configured to control the UV-ray emitting assembly to stop emitting UV rays, when the UV-ray emitting assembly is emitting UV rays to disinfect the display panel and the processor determines that the current distance is less than or equal to the preset distance.

17. The electronic device of claim 7, wherein the processor is further electrically connected to the light-emitting member and the display panel, and the processor is configured to control the light-emitting member to emit visible light to the display panel so as to display a prompt when the UV-ray emitting assembly operates.

18. The electronic device of claim 17, wherein the processor is further configured to control the prompt to move on the display panel when the UV-ray emitting assembly operates.

* * * * *